US010028921B1

(12) United States Patent
Koneru et al.

(10) Patent No.: US 10,028,921 B1
(45) Date of Patent: Jul. 24, 2018

(54) PHYTONADIONE COMPOSITIONS AND RELATED METHODS

(71) Applicant: EXELA HOLDINGS, INC, Lenoir, NC (US)

(72) Inventors: Phanesh Koneru, Lenoir, NC (US); Sreerarama Murthy Mallipeddi, Lenoir, NC (US); Jonathan E. Sterling, Lenoir, NC (US)

(73) Assignee: EXELA HOLDINGS, INC, Lenoir, NC (US)

( * ) Notice: Subject to any disclaimer, the term of this patent is extended or adjusted under 35 U.S.C. 154(b) by 0 days.

(21) Appl. No.: 15/054,797

(22) Filed: Feb. 26, 2016

Related U.S. Application Data

(60) Provisional application No. 62/121,869, filed on Feb. 27, 2015.

(51) Int. Cl.
*A61K 31/122* (2006.01)
*A61J 1/05* (2006.01)

(52) U.S. Cl.
CPC ............... *A61K 31/122* (2013.01); *A61J 1/05* (2013.01)

(58) Field of Classification Search
CPC .................................................. A61K 31/122
See application file for complete search history.

(56) References Cited

FOREIGN PATENT DOCUMENTS

WO      WO 2011153513 A2   * 12/2011   ........... A61K 9/1075

OTHER PUBLICATIONS

Drugs.com. "Phytonadione." © 2016. Available from: < https://www.drugs.com/cdi/phytonadione.html >.*
Lab Unlimited. "Eppendorf Reaction vials 5.0ml, sterile 0030122321." © 2013. Available from: < https://www.labunlimited.com/s/pg_dl_30224/4AJ-6282532/Eppendorf-Reaction-vials-5.0ml,-sterile-0030122321 >.*
"Changes in heavy metal accumulation in Enteromorpha spp. from the Gulf of Gdansk." © 1995. Oceanologia. No. 37, Issue 1, pp. 99-110.*
"Development and validation for the determination of (E)-/(Z)-vitamin K1 isomers in human plasma by LC-MS/MS." © Jun. 2013. ResearchGate. Available from: < https://www.researchgate.net/publication/308319699_Development_and_validation_for_the_determination_of_E-Z-vitamin_K1_isomers_in_human_plasma_by_LC-MSMS >.*

* cited by examiner

*Primary Examiner* — Noble E Jarrell
*Assistant Examiner* — John S Kenyon
(74) *Attorney, Agent, or Firm* — Casimir Jones, S.C.; David Casimir

(57) ABSTRACT

Stable Phytonadione compositions for parenteral administration are provided which comprise (E) isomer of phytonadione at or greater than 97% w/w as the active ingredient, and is substantially free of (Z) isomer. Said compositions are stable, sterile, and particulate-free. Further, said compositions reduce or avoid allergic reactions to benzyl alcohol and polysorbate. In some aspects, the compositions are free or substantially free of benzyl alcohol and/or reduced amounts of polysorbate. Methods of manufacture and methods of administration also provided.

12 Claims, No Drawings

PHYTONADIONE COMPOSITIONS AND RELATED METHODS

The present application claims priority to U.S. Provisional Patent Application Ser. No. 62/121,869, filed Feb. 27, 2015, the disclosure of which is herein incorporated by reference in its entirety.

FIELD OF THE INVENTION

The present invention relates to Phytonadione compositions and related methods. Accordingly, the present invention concerns the fields of pharmacy, medicine, and chemistry.

BACKGROUND

Phytonadione has been in use for several years in the United States and other countries. Phytonadione for parenteral administration has been known. Such compositions are administered to a significant number of neonatal subjects and adults. Following is a description of one such composition:

Phytonadione is 2-methyl-3-phytyl-1, 4-naphthoquinone. Its empirical formula is C31H46O2 and its structural formula is:

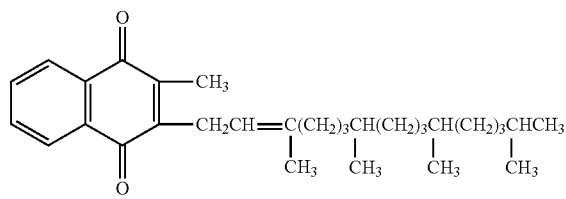

Vitamin K1 Injection (Phytonadione Injectable Emulsion, USP) of Hospira is a yellow, sterile, nonpyrogenic aqueous dispersion available for injection by the intravenous, intramuscular and subcutaneous routes. Each milliliter contains phytonadione 2 or 10 mg, polyoxyethylated fatty acid derivative 70 mg, dextrose, hydrous 37.5 mg in water for injection; benzyl alcohol 9 mg added as preservative. May contain hydrochloric acid for pH adjustment. pH is 6.3 (5.0 to 7.0). Phytonadione is oxygen sensitive.

Another composition marketed by International Medicines company is described as follows:

Phytonadione Injectable Emulsion, USP, is a yellow, sterile, aqueous colloidal solution of vitamin K1, with a pH of 3.5 to 7.0. It is available for injection by the intravenous, intramuscular, and subcutaneous route.

Each 0.5 mL contains 1 mg phytonadione (Vitamin K1), 10 mg polysorbate 80, 10.4 mg propylene glycol, 0.17 mg sodium acetate anhydrous, and 0.00002 mL glacial acetic acid. Additional glacial acetic acid or sodium acetate anhydrous may have been added to adjust pH to meet USP limits of 3.5 to 7.0. The air above the liquid in the individual containers has been displaced by flushing with nitrogen during the filling operation.

Both these compositions are known to cause serious adverse events such as anaphylactic reactions. One of the currently marketed products has the following black box warning in its product labeling:

Severe reactions, including fatalities, have occurred during and immediately after INTRAVENOUS injection of phytonadione, even when precautions have been taken to dilute the phytonadione and to avoid rapid infusion. Severe reactions, including fatalities, have also been reported following INTRAMUSCULAR administration. Typically these severe reactions have resembled hypersensitivity or anaphylaxis, including shock and cardiac and/or respiratory arrest. Some patients have exhibited these severe reactions on receiving phytonadione for the first time. Therefore the INTRAVENOUS and INTRAMUSCULAR routes should be restricted to those situations where the subcutaneous route is not feasible and the serious risk involved is considered justified.

It is unclear whether the anaphylactic reaction is caused by the drug itself, or one or more of the excipients, or their combination. For example, polysorbate, polyethoxylated fatty acids are known to have caused adverse events. Benzyl alcohol and propylene glycol are known to be toxic to pediatric patients. Despite the fact that phytonadione has been on the market at least since 1983, there have been no product improvements in an attempt to reduce the adverse events. This effort is complicated by the fact that phytonadione is oxygen-sensitive, and is insoluble in water. Thus, formulation and process-related issues become very significant. There is a need to provide alternate formulations of phytonadione to alleviate some potentially dangerous adverse events. Without wishing to be bound to any theory or mechanism of action, such formulations are presented herein.

SUMMARY OF THE INVENTION

In some embodiments, provided herein is a stable sterile phytonadione parenteral composition that comprises predominantly (E) isomer of Phytonadione as the active principle, wherein the (E) isomer is present at a concentration of from about 0.1 mg/ml to 20 mg/ml, the (Z) isomer is present at less than 3% w/w; preferably, less than 2% w/w or less than 1% w/w; or preferably, less than 0.5% w/w. In one aspect, the composition is completely free of a preservative such as benzyl alcohol. Benzyl alcohol quantitation in a pharmaceutical formulation is known in the art. See for example, USP <51>("Preservative Effectiveness Test, USP 37-NF-32."), which is incorporated by reference herein. In some embodiments, the composition is provided in a prefilled syringe or in a vial.

For example, in some embodiments, provided herein are compositions comprising phytonadione in its (E) isomer form that is substantially free of its (Z) isomer. In some embodiments, the composition is provided in aqueous form. In some embodiments, the composition is particulate-matter-free. In some embodiments, the composition is sterile. In some embodiments, the composition is configured to be injectable into a mammal. In some embodiments, the composition is one or more or all of stable, injectable, sterile, particulate-matter-free, and aqueous. In some embodiments, the phytonadione is at a concentration of from about 100 ug/ml to about 20 mg/ml. In some embodiments, the composition further comprises a pH adjuster. In some embodiments, the composition has a pH of from about 3.5 to about 8.0. In some embodiments, the (Z) isomer is present from about 0.5% to less than or equal to about 3% w/w of the (E) isomer. In some embodiments, the composition is free of benzyl alcohol. In some embodiments, the composition is free of or substantially free of cremophor and/or propylene glycol. In some embodiments, the composition comprises less than 20 mg/ml of polysorbate. In some embodiments, the composition is provided in a container suitable for storage, shipment, and/or use of the composition in medical context. For example, in some embodiments, the composition is provided in a non-reacting glass or non-reacting polymeric container selected from a vial container or a pre-filled syringe container. In some embodiments, the container is made of polyethylene or polypropylene or a combination thereof. In some embodiments, an epoxide derivative of the (E) isomer of phytonadione is present at less than 4% w/w of the (E) isomer.

Further provided herein are uses of any of the above compositions or other compositions described herein. For example, in some embodiments, provided herein are uses for the treatment or prevention of a disease or condition.

In some embodiments, provided herein are methods of administering any of the above compositions or other compositions described herein to a mammal (e.g., a human). In some embodiments, the method comprises a method of reducing the potential for anaphylactic reaction associated with phytonadione administration comprising: administering a composition comprising Phytonadione in its (E) isomer form that is substantially free of its (Z) isomer, at a concentration of from about 0.1 mg/ml to about 20 mg/ml; and optionally a pH adjuster, wherein the composition has a pH of from about 3.5 to about 8.0, wherein said (Z) isomer is present at about 3% w/w or less of the (E) isomer; and wherein said composition is free of benzyl alcohol and a polysorbate at a concentration of less than about 20 mg/ml. In some embodiments, the composition is administered from a vial or a pre-filled syringe wherein the vial or pre-filled syringe is selected from a non-reacting glass or polymeric material.

DETAILED DESCRIPTION

It is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a container" includes one or more of such containers and reference to "the agent" includes reference to one or more of such agents. In describing and claiming the present invention, the following terminology will be used in accordance with the definitions set forth below.

As used herein, "Phytonadione" refers to a synthetic molecule described above. The (E) and (Z) isomer structures are known in the art. Under no circumstances, Phytonadione as used herein does not encompass synthetically radioisotope-labeled molecule (i.e., molecules that contain added radioisotopes beyond any that may be naturally present in a population of molecules).

As used herein, "subject" refers to a mammal. Examples of subjects include humans, and may also include other animals such as horses, pigs, cattle, dogs, cats, rabbits, and aquatic mammals.

As used herein, the term "particulate-matter-free" or its grammatical equivalents refer to the state in which the composition meets the USP requirements for particulate matter in parenteral solutions or emulsions. See for example, USP XXXII, Chapter 788. One of skill in the art understands and knows how to assess whether a given composition meets USP particulate matter requirements.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include individual values and sub-ranges within the indicated range. Thus, included in this numerical range are individual values such as 2, 3, 4, 5, 10, 14, 15, 20, 23, 25, 30, 35, 38, 40, 44, 45, 48 and sub-ranges such as from 2-3, from 2-4, from 5-10, from 5-20, from 5-25, from 5-30, from 5-35, from 5-40, from 5-50, from 2-10, from 2-20, from 2-30, from 2-40, from 2-50, from 10-15, from 10-20, from 10-30, from 10-40, from 10-50, from 20-30, from 20-25, from 20-40, from 20-50, etc. This same principle applies to ranges reciting only one numerical value as a minimum or a maximum. Furthermore, such an interpretation should apply regardless of the breadth of the range or the characteristics being described. In some aspects, the term "about" may refer to +/−10% of a recited value, depending on the context as is customary in the art.

As noted in the Background section, current phytonadione formulations carry several adverse events. A careful review was undertaken by present inventors in an attempt to minimize some of the adverse events. It included evaluation of the drug substance, its impurity profile, the excipients, composition of parenteral phytonadione formulations, and the manufacturing process of phytonadione compositions. In that attempt, it has been discovered that the formulation, the drug substance, and the manufacturing process, all could be improved.

First, with respect to the drug substance: Phytonadione may exist as a mixture of two isomers, known as (E) and (Z) isomers. The precise ratio of these isomers in a given drug product composition is unknown. Some commercial preparations may contain up to 20% of the cis (Z) isomer. See for example, Budavari, S. (ed.). The Merck Index—Encyclopedia of Chemicals, Drugs and Biologicals. Rahway, N.J.: Merck and Co., Inc., 1989., p. 1580. Commercially available phylloquinone (phytonadione) is prepared synthetically and may contain not only 2',3'-trans-phylloquinone (not less than 75%), but also 2',3'-cis-phylloquinone (up to 21% as per USP XXXII).

One complication is that the relative pharmacologic activity of the two isomers is not precisely known. However, it is generally known that the (E) isomer is presumed to possess majority of or most of the activity of the Phytonadione composition. There are conflicting reports as to the activity of the (Z) isomer. There has been no known phytonadione drug product composition that is substantially free of the (Z) isomer. Another impurity associated with phytonadione products is the epoxide derivative of each of the (Z) and (E) isomers. The trans-epoxyphylloquinone is suspected at about 4.0 percent. It has been determined herein that phytonadione compositions that contain substantially isomerically pure (E) isomer of phytonadione are advantageous. In one aspect, the (E) isomer comprises from about 95% to about 99.9% of the active substance; in another aspect, the (E) isomer is from about 98% to 99.5%; in another aspect, the (E) isomer is from 99% to 99.95%. By increasing the isomeric purity of the drug substance, the total content of the drug substance in the drug product has been reduced. For example, the drug substance of the drug product is now an (E)-isomer that is present at from about 100 ug/ml to about 20 mg/ml. In some aspects, the (E) isomer is from about 500 ug/ml to about 10 mg/ml, while simultaneously, the (Z) isomer in the composition is less than about 3%. One or methods to determine the (Z) isomer levels are known in the art. See for example, USP XXXVII phytonadione monograph, which is incorporated by reference.

Isomerically pure (E)-isomer composition may be prepared, for example by solvent extraction, partition chromatography, distillation, and column chromatography, or a combination thereof.

One or more methods to determine the (E) isomer levels for assay purposes are known in the art. See for example, USP XXXVII phytonadione monograph, which is incorporated by reference.

With respect to excipients: The International Medicines formulation contains 20 mg/ml of polysorbate 80 and 20.8 mg/ml of propylene glycol. Polysorbate 80 is suspected to be causing anaphylactic reactions. Propylene glycol is considered not desirable in pediatric formulations. On the other hand, the formulation by Hospira contains polyoxyethylated fatty acid derivative as a solubilizer and benzyl alcohol as a preservative. Polyoxyethylated fatty acid derivatives are suspected of causing anaphylactic reactions while also causing neurological and nephrological toxicities. Benzyl alcohol is recommended to be removed from pediatric patient formulations.

However, finding a substitute solubilizer is difficult due to the highly insoluble nature of phytonadione in water and many other commonly used solvents. After much work, it has been determined that polysorbate concentration in the formulation can be reduced. For example, in certain cases, the polysorbate (which can be either Polysorbate 80 or Polysorbate 20, or other versions and mixtures thereof) in the composition is reduced to the extent that the polysorbate: (E) isomer of phytonadione is less than 1:10; in some aspects, the ratio is less than 1:9; or less than 1:8; or less than 1:7; or less than 1:6; or less than 1:5; or less than 1:4; or less than 1:3; or less than 1:2; or less than 1:1. In some aspects, the total polysorbate in the composition is less than about 70 mg/ml; or less than about 60 mg/ml; or less than about 50 mg/ml; or less than about 40 mg/ml; or less than about 30 mg/ml; or less than about 20 mg/ml; or less than about 10 mg/ml; or less than about 5 mg/ml; or less than about 4 mg/ml; or less than about 3 mg/ml; or less than about 2 mg/ml. In some cases, the polysorbate is at least 0.1 mg/ml. Any composition with polysorbate concentration in the ranges stated in the previous sentences is within the scope of this invention. Thus, in many cases, a 20-40% reduction, or even 50-60%, or 70-80%, or even up to 90% reduction is achieved in that excipient. Thus, one unexpected advantage of reducing the total concentration of the drug substance is the ability to reduce the concentrations of the solubilizing agents that are considered to be undesirable.

With respect to the manufacturing process, the following considerations apply. Phytonadione is known to be oxygen-sensitive and light-sensitive. In some embodiments, provided herein are compositions that have in some aspects higher than previously known (E) isomer concentrations. Therefore, extra care should be taken to at least meet a specification of less than 4%, but preferably, the (E) epoxide should be less than 3%, or less than 2%, or less than 0.5%.

One difficulty is that the phytonadione compositions are preferably sterilized using heat. In that case, the probability of raising the (E)-epoxide levels is high.

Therefore, in some embodiments, to reduce the probability of increasing impurities in the formulations, the oxygen in the container containing the phytonadione composition is removed by way of replacement with nitrogen or argon or another inert gas. The replacement is done using traditional methods such as blowing with an inert gas and then sealing the container. Alternatively, the phytonadione containers are first evacuated and then filled with an inert gas, and then sealed. In one aspect, the phytonadione containers are subjected to temperatures less than 2-8° C., or in some aspects minus 10° C. or less, or in some aspects minus 20° C. or less, or in some aspects minus 30° C. or less, and then evacuated, and then sealed, or alternatively, filled with an inert gas after evacuation, and then sealed. The compositions contain in some aspects less than 3% of the total impurities. Phytonadione parenteral compositions are provided that comprise, consist of, or consist essentially of an isomerically pure drug substance, namely a drug substance that is greater than about 97%, or greater than about 98%, or greater than about 99% of the (E) isomer of Phytonadione, but in all cases contain less than 100% of the (E) isomer. In one aspect, the composition comprises (E)-isomer of Phytonadione about 98% w/w, and a pharmaceutically acceptable carrier suitable for parenteral administration. In one aspect, the composition comprises from about 100 ug/mL to about 20 mg/mL of Phytonadione as its (E) isomer, and comprises only about 3.0% to about 0.5% of its (Z) isomer. The carrier may include: a tonicity agent in sufficient concentration to make the composition isotonic. Examples of tonicity agents include, but not limited to, sodium chloride, mannitol, sorbitol, dextrose, or organic solvents such as ethanol, glycerin, sorbitol, etc., or a combination thereof. The carrier may optionally include a pH adjustor or a buffering agent. Some examples of such agents include: sodium hydroxide, hydrochloric acid, citrate, acetate, tartrate, and phosphate buffers/buffering agents. In one aspect, the composition has a pH of from about 3.5 to about 8.

In one embodiment, a Phytonadione composition that is ready to administer to the patient is provided. In another embodiment the Phytonadione composition is injected intravenously, intramuscularly, or subcutaneously both in pediatric and adult patients. In some embodiments, the composition is provided to the subject by slow infusion. In one aspect, a Phytonadione ready-to-administer injectable composition that is sterilized using steam or super-heated water is provided. In yet another aspect, an aqueous Phytonadione ready to administer parenteral composition that is prepared by aseptic filtration sterilization. The present ready to use Phytonadione injectable composition could be terminally sterilized and commercially produced in large quantities for commercial distribution. Terminal sterilization can be accomplished in a suitable sterilizer employing steam, superheated water, or a combination thereof (generally known as heat sterilization). The appropriate sterilization conditions can be determined based on the number of units and the size of the units to be sterilized. In one aspect, sterilization is conducted in an air over-pressure type sterilizer or steam sterilizer or water cascade type sterilizer commercially available. Exemplary time and temperature levels required for adequate sterilization is to achieve and maintain a temperature of about 121 degrees C. for from about 7-8 minutes to about 30 minutes or more as needed. Rotisserie autoclave/shaking of vials immediately after removing from the autoclave.

It should be recognized that even though the current compositions are terminally sterilizable, under certain conditions, the compositions may be sterilized aseptically. Such aseptic sterilization may include filtration or radiation methods, which are well-known in the art.

In one aspect, the compositions are not isotonic. For example, compositions for subcutaneous administration may not need to be isotonic. In such cases, the compositions may or may not include a tonicity agent. Such compositions are also within the scope of this invention. When needed, the present formulations include a tonicity agent. Suitable tonicity agents may be selected from a number of tonicity agents. Exemplary agents include without limitation: sodium chloride, mannitol, sorbitol, dextrose, or organic solvents such as ethanol, glycerin, sorbitol, etc., or a combination thereof, or their equivalents. One of skill in the art is aware of making compositions isotonic using a tonicity agent such as sodium chloride or dextrose or their equivalents. Examples of such equivalents include but not limited to mannitol, sorbitol, and glycerin. See for example, Remington: The Science and Practice of Pharmacy, 19$^{th}$ Ed., 1995, 613-27. In one embodiment, an isotonic solution can have an osmotic pressure of about 250-350 mOsmol/Kg.

In some embodiments, the pH of the compositions may be unadjusted, or adjusted so that the composition may have a pH ranging from about 3.5 to about 8.0. When the pH is to be adjusted, a suitable pH adjuster such as sodium hydroxide, potassium hydroxide, hydrochloric acid, sulfuric acid, or organic pH adjustors such as cysteine, lysine, acetic acid, citric acid, may be used.

An appropriate concentration of acid or base may be from about 0.1M to 1M or more. The compositions may be supplied in a glass vial, preferably amber vial (for example, Type II) or pre-filled syringes or in a plastic container made from polyethylene, polypropylene or a combination thereof. The container may range in size from about 0.5 ml to 10 ml. In another aspect, one or all of the compositions of the invention are sterile, substantially particulate-matter-free. In another aspect, one or all of the compositions are stable. For example, in addition to being particulate-matter-free, the compositions retain at least 95% of the original amount of Phytonadione after having been stored at 60° C. for one week. Additionally provided is a container including a terminally sterilized stable ready to administer Phytonadione injectable composition comprising, consisting of, or consisting essentially of a (E)-Phytonadione, at a concentration of about 100 ug/ml to 20 mg/ml, either sodium chloride, dextrose, or mannitol as a tonicity agent at a concentration sufficient to make the composition isotonic, and a pH adjuster or a buffer to provide the composition a pH of from about 3.5 to about 8.0.

EXAMPLE EMBODIMENTS

Some of the exemplary formulations of the present invention are shown in Tables 1-2 as follows:

TABLE 1

| Ingredients | Formulation 1 | Formulation 2 | Formulation 3 |
|---|---|---|---|
| Phytonadione E-isomer (Phytonadione) | 2.0 mg | 1.6 mg | 9.0 mg |
| Polyoxyethylated fatty acid derivative (Cremophor EL) | 14 mg | 21 mg | 60 mg |
| Dextrose, monohydrate | 46.4 mg | 46 mg | 40 mg |
| Benzyl alcohol (preservative) | — | — | — |
| Hydrochloric acid/ Sodium hydroxide | q.s. to pH 5-7 | q.s. to pH 3.5-7.0 | q.s. to pH 3.5-7.0 |
| Water for injection | q.s. to 1 mL | q.s. to 1 mL | q.s. to 1 mL |

TABLE 2

| Ingredients | Formulation 4 | Formulation 5 | Formulation 6 | Formulation 7 |
|---|---|---|---|---|
| Phytonadione E-isomer (Phytonadione) | 1.8 mg | 10 mg | 1.0 mg | 2.0 mg |
| Polyborbate 80 | 15 mg | 70 mg | — | — |
| Polysorbate 20 | — | — | 8 mg | 15 mg |
| Dextrose, monohydrate | 32 mg | 32 mg | — | — |
| Sorbitol | — | — | — | 5.0% w/v |
| Ethanol (100%) | — | — | 2.0% v/v | — |
| Hydrochloric acid/Sodium hydroxide | q.s. to pH 5-7 | q.s. to pH 4.0-6.0 | q.s. to pH 3.5-7.0 | q.s. to pH 5-7 |
| Water for injection | q.s. to 1 mL | q.s. to 1 mL | q.s. to 1 mL | q.s. to 1 mL |

General Procedure to Manufacture:

Important Note: Carry out all the steps in yellow light.

1. Weigh the required quantity of Polyoxyethylated fatty acid derivative (Cremophor EL) into a beaker and warm to about 60° C.
2. Weigh the required quantity of Phytonadione E-isomer (Phytonadione) and transfer into the above liquefied Polyoxyethylated fatty acid derivative (Cremophor EL) or Polysorbate and mix sell for about 30 minutes.
3. If Benzyl alcohol is present in the formulation, add the same to the above and mix.
4. In a separate beaker, prepare dextrose solution by dissolving Dextrose monohydrate in water for injection.
5. While mixing, slowly add the dextrose solution or Sorbitol or Ethanol to the Phytonadione mix and stir for about 30 minutes.
6. Check the pH of the emulsion and adjust to the required pH with Hydrochloric acid/Sodium hydroxide. Finally, adjust the volume of the final formulation with Water for Injection and stir.
7. Filter the final formulation from 0.2 uM filter and fill 0.5/1.0 mL portions into 2 mL amber vials or 1 mL pre-filled syringes.
8. Sterilize the filled containers in autoclave at 121° C. for about 30 minutes.
9. Immediately after unloading the vials from the sterilizer, shake the vials in the autoclave trays.

Methods of Administration

In one aspect, Phytonadione is administered by a caregiver such as a nurse, nurse practitioner, physician, physician assistant, or another healthcare personnel. The caregiver is provided with instructions by way of a patient guide, medication guide, drug product labeling, or verbal instructions that the Phytonadione compositions may be administered.

In one aspect, the compositions are provided to a subject in need thereof with a composition in a container that is amenable to deliver the ready to use composition. Said container is provided in a 1 ml, 2 ml, 5 ml, 10 ml, glass or plastic vial. Alternatively, a ready-to-administer composition may be provided in a pre-filled syringe. Such pre-filled syringes are able to deliver drug solution volumes from about 0.1 ml to about 10 ml. For example, about 0.1 ml, 0.2 ml, 0.25 ml, 0.3 ml, 0.4 ml, 0.5 ml, 0.75 ml, 1.0 ml, 1.25 ml, 1.5 ml, 2.0 ml, 3.0 ml, 5.0 ml, 10 ml, of drug solution volume can be delivered to patients.

In all cases, the containers of said vials or pre-filled syringes may be made of non-reacting glass, or non-reacting polymeric material such as polypropylene or polyethylene or a mixture thereof. Several non-reacting containers are known in the art. The non-reacting containers described herein include not only the vial or pre-filled syringe that makes up the bulk of the container structure, but also any other part of the container that comes in contact with the drug solution, such as stoppers, plungers, etc. These also are made of non-reacting glass or polymeric materials.

In one aspect the Phytonadione composition is administered intramuscularly. In another aspect, the Phytonadione compositions are administered subcutaneously or intravenously. Phytonadione is useful in the following coagulation disorders which are due to faulty formation of factors II, VII, IX and X when caused by vitamin K deficiency or interference with vitamin K activity:

anticoagulant-induced prothrombin deficiency caused by coumarin or indanedione derivatives;
prophylaxis and therapy of hemorrhagic disease of the newborn;
hypoprothrombinemia due to antibacterial therapy;
hypoprothrombinemia secondary to factors limiting absorption or synthesis of vitamin K, e.g., obstructive jaundice, biliary fistula, sprue, ulcerative colitis, celiac disease, intestinal resection, cystic fibrosis of the pancreas, and regional enteritis;
other drug-induced hypoprothrombinemia where it is definitely shown that the result is due to interference with vitamin K metabolism, e.g., salicylates.

Phytonadione of the present invention is useful for prophylaxis of hemorrhagic disease of the newborn. The American Academy of Pediatrics recommends that vitamin K1 be given to the newborn. A single intramuscular dose of phytonadione 0.5 to 1 mg within one hour of birth is recommended.

Phytonadione of the present invention is also useful for treatment of hemorrhagic disease of the newborn. A prompt response (shortening of the prothrombin time in 2 to 4 hours) following administration of vitamin K1 is usually diagnostic of hemorrhagic disease of the newborn, and failure to respond indicates another diagnosis or coagulation disorder. (E)-isomer of phytonadione up to 1 mg should be given either subcutaneously or intramuscularly. Higher doses may be necessary if the mother has been receiving oral anticoagulants. Whole blood or component therapy may be indicated if bleeding is excessive. This therapy, however, does not correct the underlying disorder and phytonadione should be given concurrently.

The (E)-isomer compositions of phytonadione described herein are also useful to treat anticoagulant-induced prothrombin deficiency in adults. To correct excessively prolonged prothrombin time caused by oral anticoagulant therapy—up to 2.5 to 10 mg or up to 25 mg initially is recommended. In rare instances up to 50 mg may be required. Frequency and amount of subsequent doses should be determined by prothrombin time response or clinical condition. If in 6 to 8 hours after parenteral administration the prothrombin time has not been shortened satisfactorily, the dose should be repeated.

The (E) isomer compositions of phytonadione are useful to treat hypoprothrombinemia due to other causes in adults. A dosage of 2.5 to 25 mg or more (rarely up to 50 mg) is recommended, the amount and route of administration depending upon the severity of the condition and response obtained.

In some embodiments, a composition is administered to a subject that has previously had an adverse reaction to other Phytonadione compositions or that is suspected or known to be at risk for an adverse reaction (e.g., based on genetics, family history, etc.).

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

We claim:

1. A stable, injectable, sterile, particulate-matter-free, aqueous phytonadione composition comprising Phytonadione in its (E) isomer form that has less than or equal to 3% w/w of its (Z) isomer, at a concentration of from about 100 ug/ml to about 20 mg/ml; and optionally a pH adjuster, wherein the composition has a pH of from about 3.5 to about 8.0.

2. The composition of claim 1, wherein said (Z) isomer is present from 0.5% to less than or equal to 3% w/w of the (E) isomer.

3. The composition of claim 1, wherein said composition is free of benzyl alcohol.

4. The composition of claim 1, wherein said composition is free of cremophor and propylene glycol.

5. The composition of claim 1, wherein the composition comprises less than 1:10 ratio of (E)-isomer of phytonadione:polysorbate.

6. The composition of claim 1, wherein said composition is provided in a non-reacting glass or non-reacting polymeric container selected from a vial container or a pre-filled syringe container.

7. The composition of claim 6, wherein the non-reacting polymeric container is made of polyethylene or polypropylene or a combination thereof.

8. The composition of claim 1, wherein an epoxide derivative of the (E) isomer of phytonadione is present at less than 4% w/w of the (E) isomer.

9. A method comprising: administering the composition of claim 1 to a mammal.

10. The method of claim 9, wherein the mammal is a human.

11. A method of reducing the potential for anaphylactic reaction associated with phytonadione administration comprising: administering a composition to a patient in need thereof, the composition comprising Phytonadione in its (E)

isomer form that has less than or equal to 3% w/w of (Z) isomer, at a concentration of from about 100 ug/ml to about 20 mg/ml; and optionally a pH adjuster, wherein the composition has a pH of from about 3.5 to about 8.0, and wherein said composition is free of benzyl alcohol and wherein the composition comprises polysorbate at a concentration of less than about 1:10 ratio of (E) isomer of phytonadione:polysorbate.

12. The method of claim 11, wherein the composition is administered from a vial or a pre-filled syringe wherein the vial or pre-filled syringe is selected from a non-reacting glass or polymeric material.

* * * * *